(12) United States Patent
Choi et al.

(10) Patent No.: US 9,393,308 B2
(45) Date of Patent: Jul. 19, 2016

(54) MICELLE STRUCTURE OF NANO PREPARATION FOR DIAGNOSIS OR TREATMENT OF CANCER DISEASE AND PREPARATION METHOD THEREOF

(71) Applicant: KOREA ADVANCED INSTITUTE OF SCIENCE AND TECHNOLOGY, Daejeon (KR)

(72) Inventors: Chulhee Choi, Daejeon (KR); Kyuha Chong, Seoul (KR); Jiho Park, Daejeon (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 71 days.

(21) Appl. No.: 14/315,943

(22) Filed: Jun. 26, 2014

(65) Prior Publication Data

US 2015/0148428 A1 May 28, 2015

(30) Foreign Application Priority Data

Nov. 22, 2013 (KR) .......................... 10-2013-0143045

(51) Int. Cl.
*A61K 47/24* (2006.01)
*A61K 31/122* (2006.01)
*A61K 9/107* (2006.01)

(52) U.S. Cl.
CPC ............... *A61K 47/24* (2013.01); *A61K 9/1075* (2013.01); *A61K 31/122* (2013.01)

(58) Field of Classification Search
CPC .... A61K 47/24; A61K 31/122; A61K 9/1075
See application file for complete search history.

(56) References Cited

U.S. PATENT DOCUMENTS 6,123,923 A * 9/2000 Unger ................. A61K 49/0002
424/450
2004/0013717 A1 1/2004 Allen et al.

OTHER PUBLICATIONS

Stummer, W. et al., "Fluorescence-guided surgery with 5-aminolevulinic acid for resection of malignant glioma: a randomised controlled multicentre phase III trial," The lancet oncology, 2006, 7 (5), 292-401.
Stupp, R. et al., "Radiotherapy plus Concomitant and Adjuvant Temozolomide for Glioblastoma," New England Journal of Medicine, 2005, 352, 987-996.
Sarin, H. et al., "Effective transvascular delivery of nanoparticles across the blood-brain tumor barrier into malignant glioma cells," Journal of Translational Medicine, 2008, 6 (1) 80.
Chauhan, V.P. et a., "Normalization of tumour blood vessels improves the delivery of nanomedicines in a size-dependent manner," Nature Nanotechnology, 2012, 7 (6) : 383-388.
Vikash P. Chauhan, et al., "Normalization of tumour blood vessels improves the delivery of nanomedicines in a size-dependent manner," Nature Nanotechnology, vol. 7, Jun. 2012, 6 pages.
Kyuha Chong, et al., "Enhancement of the photocytotoxic efficiency of sub-12-nm therapeutic polymeric micelles with increased co-localisation in mitochondria," Dec. 2013, 14 pages.

* cited by examiner

*Primary Examiner* — Wu-Cheng Winston Shen
*Assistant Examiner* — Christopher R Stone
(74) *Attorney, Agent, or Firm* — Fredikson & Byron, P.A.

(57) ABSTRACT

Disclosed herein are a nanopreparation having a micelle structure for diagnosis or treatment of cancer diseases, and a method of preparing the same, and more particularly, a nanopreparation having a micelle structure available for diagonosis or treatment of cancer diseases and a method for preparing the same, wherein the nanopreparation is prepared by encapsulating a photosensitizer by forming micelle with polymeric lipid DSPE-mPEG. The nanopreparation having the micelle structure according to the present invention has a size of 12 nm or less by encapsulating hypericin, which is a photosensitizer, by forming micelle with polymeric lipid DSPE-mPEG having a molecular weight of 1500 to 2500. Resultingly, the nanopreparation easily overcomes a blood-tumor barrier (BTB) and an interstitial fluid pressure and has light induced cytotoxicity efficiency that is about more than 2.5 times higher than that of the case where hypericin is used alone.

5 Claims, 8 Drawing Sheets

Fig. 4
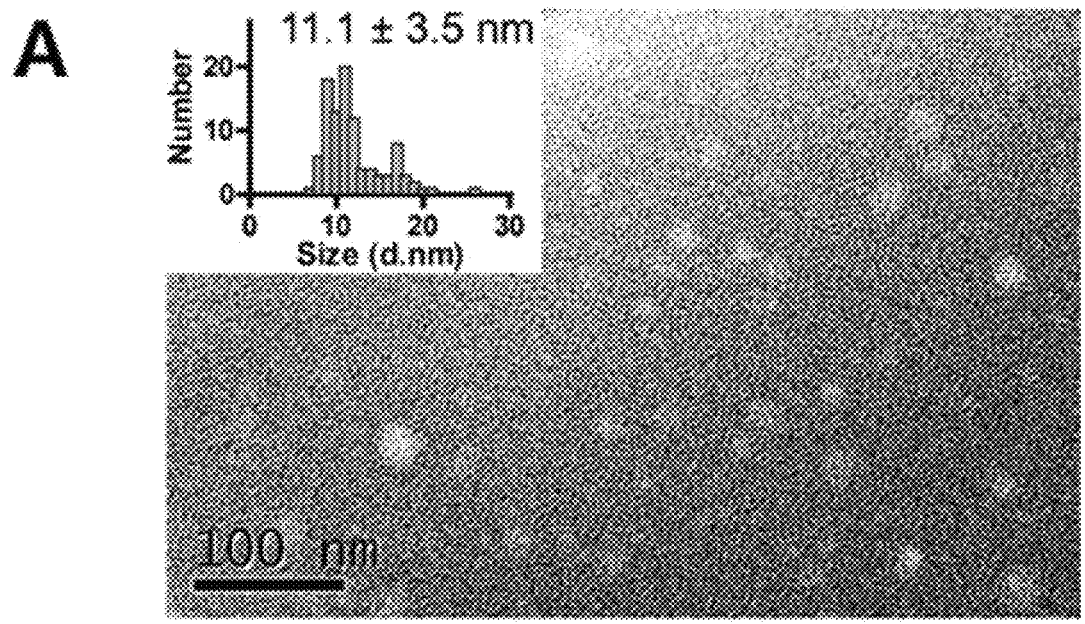
A
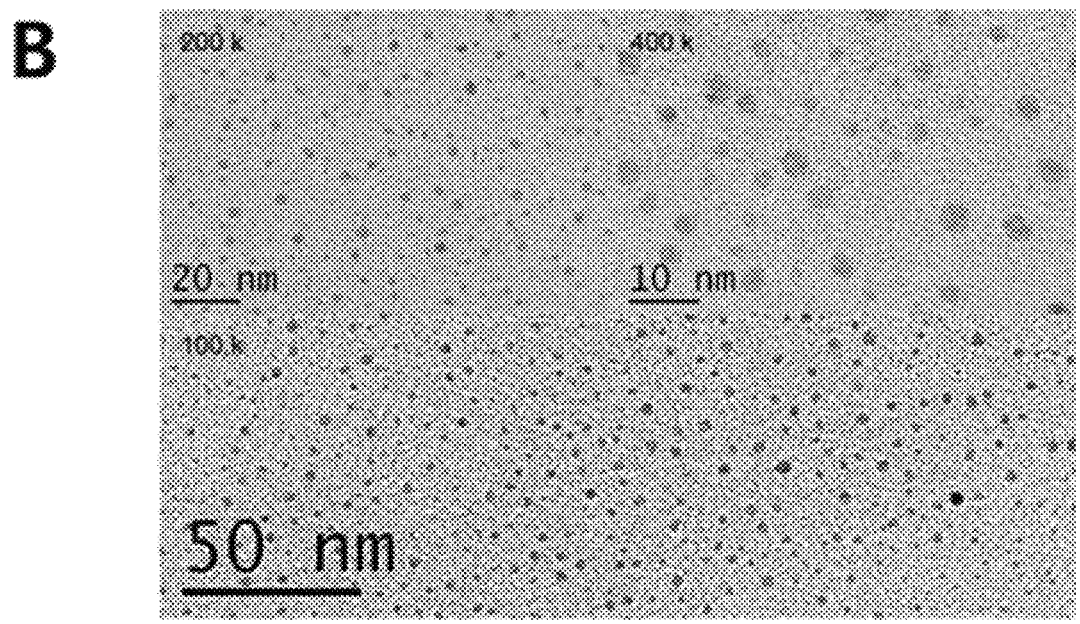
B

MICELLE STRUCTURE OF NANO PREPARATION FOR DIAGNOSIS OR TREATMENT OF CANCER DISEASE AND PREPARATION METHOD THEREOF

CROSS-REFERENCES TO RELATED APPLICATION

This patent application claims the benefit of priority from Korean Patent Application No. 10-2013-0143045, filed on, 22 Nov. 2013, the contents of which are incorporated herein by reference.

BACKGROUND OF THE INVENTION

1. Field of the Invention

The present disclosure relates to a nanopreparation having a micelle structure for diagnosis or treatment of cancer diseases, and a method of preparing the same, and more particularly, to a nanopreparation having a micelle structure available for diagnosis or treatment of cancer diseases, and a method of preparing the same, wherein the nanopreparation is prepared by encapsulating anti-cancer drug, such as a photosensitizer, by forming micelle with polymeric lipid DSPE-mPEG.

2. Description of the Related Art

Photodynamic therapy is one of currently promising method for treating cancers. Photodynamic therapy is a therapeutic method using a following principle: when a photosensitizer, which is a material sensitive to light, is administered to the body, singlet oxygen or free radicals are generated due to a chemical reaction which is induced by external light in the case where light having a particular wavelength is irradiated from the outside; and then, the singlet oxygen or free radicals induce apoptosis of various lesion sites or cancer cells to destroy them.

Photodynamic therapy is advantageous in that: only cancer cells can be selectively removed, while normal cells are retained. Due to the aforementioned advantages, photodynamic therapy has been studied in earnest from the 1980s, and clinical trials have been approved in Canada, Germany, and Japan in the 1990s. Thereafter, photodynamic therapy has been extensively used around the globe, for example, US FDA approved photodynamic therapy for esophagus cancer treatment in January 1996 and for early stage lung cancer treatment in September 1997.

Since a photosensitizer same as the photosensitizer used in photodynamic therapy can be frequently used even in photodynamic diagnosis, the photosensitizer is useful as a diagnostic and therapeutic agent of cancers. Photodynamic diagnosis has advantages in that: cancer diagnosis can be easily performed by using relatively simple equipment using optics without costly equipment such as computed tomography (CT) or magnetic resonance imaging for diagnosis of cancers; time consumption required to recognize the location or degree of cancers during an operation can be reduced; and real-time diagnosis can be performed as direct visual information is provided without an additional time for imaging. Accordingly, photodynamic diagnosis comes into the spotlight as a useful tool helping successful surgical removal of cancer. Usefulness of surgical removal using fluorescence of a photosensitizer was reported by W. Stummer, et al. in 2006 through clinical data (see Non-patent Documents 1). As such, active clinical application for diagnosis and surgical treatment of cancers has been made over regions ranging from Europe, as a starting point, to the US in 2000s in practice.

Glioblastoma holding 52% of a brain tumor is the most malignant tumor among the whole primary brain tumors. A five-year survival rate of glioblastoma is 5% or less. Glioblastoma is a fatal disease having an average survival time of 14 to 16 months even though aggressive and active treatment is performed. In the latest standard treatment of glioblastoma, concurrent chemoradiotherapy is performed after surgical removal. The standard treatment is based on the research result reported by the R. Stupp research team in 2005 in which the concurrent chemoradiotherapy using temozolomide prolongs an average survival time by 20.7% (see Non-patent Document 2). However, the therapeutic method has a problem in that the substantial average survival time can be prolonged by only 12.1 to 14.6 months. Accordingly, various therapeutic methods have been developed recently, followed by experimental and clinical attempts.

Various therapeutic methods for treating brain tumors have a problem in that a drug delivery system is less effective due to low drug permeability caused by a blood-brain barrier (BBB) and a blood tumor barrier (BTB) present in a brain; and a decrease in ability to deliver drug caused by an increase in pressure in tissue according to volumes and properties of brain tumors itself. However, an appearance of a drug delivery system using nanoparticles provides an epoch-making changeover in terms of drug delivery systems, wherein, the nanoparticles have advantages of prolonging a blood half-life, a reduction in toxicity to non-target organs, and significance of target organs or drug property modification according to feasibility of various surface modifications.

An effect of the drug delivery system using the nanoparticles is known to be decided by variables such as the size and physical properties of nanodrugs and an interrelationship between nanodrugs and brain tumor tissue or cells. Recently, the H. Sarin research team of National Institutes of Health in the US and the R. Jain research team of Harvard University have reported the research result that the size of the nanodrug used in brain tumors is suitably 12 nm or less to overcome a blood-tumor barrier (BTB) and interstitial fluid pressure in tissue (see Non-patent Documents 3 and 4). In consideration of the aforementioned research results, researches regarding adjustment of the size of the nanodrug are increasingly demanded in that the currently developed nanodrugs used to treat the brain tumor have the size of 20 nm or more.

Therefore, the present inventors have studied nanodrugs for photodynamic diagnosis or treatment, which may be used in brain tumors, resulting in the finding that a nanopreparation prepared by using hypericin as a photosensitizer and polymeric lipid DSPE-mPEG having a molecular weight of 1500 to 2500 has a size of 12 nm or less, light-induced cytotoxicity efficiency that is about more than 2.5 times higher than that of the case where only hypericin is used, and an improved relative coexistence coefficient to a mitochondrion among intracellular organelles of cancer, thereby completing the present invention.

PRIOR ART DOCUMENT

Non-Patent Document (Non-Patent Document 1) W. Stummer, M. D., et al., The lancet oncology., 2006, 7(5), 392-401;
(Non-Patent Document 2) Roger Stupp, M. D., et al., N. Engl. J. Med., 2005, 352, 987-996;
(Non-Patent Document 3) H. Sarin, et al., J. Translational Med., 2008, 6 (1), 80;

(Non-Patent Document 4) Rakesh K. Jain, et al., Nature Nanotechnology, 2012, 7 (6): 383-388.

SUMMARY OF THE INVENTION

One object of the present invention is to provide a nanopreparation having a micelle structure for diagnosis or treatment of cancer diseases.

Another object of the present invention is to provide a method of preparing a nanopreparation having a micelle structure.

In order to achieve the objects, the present invention provides a nanopreparation having a micelle structure for diagnosis or treatment of cancer diseases, the nanopreparation including:

1.0 molar ratio of a photosensitizer; and
5.0 to 15.0 molar ratio of polymeric lipid DSPE-mPEG.

The present invention also provides a method of preparing a nanopreparation having a micelle structure, the method including:

mixing a photosensitizer and polymeric lipid DSPE-mPEG dissolved in an organic solvent at a molar ratio of 1.0:5.0 to 15.0 to prepare a mixed solution (step 1);

removing the organic solvent from the mixed solution prepared in the step 1 and drying the resultant to prepare a polymeric lipid film (step 2);

hydrating the polymeric lipid film prepared in the step 2 in one or more solutions selected from the group consisting of water, PBS, HBS, and HBG at room temperature to 100° C. to form nanoparticles having the micelle structure (step 3); and filtering the nanoparticles having the micelle structure formed in the step 3 to homogenize (step 4).

The nanopreparation having the micelle structure according to the present invention, has a size of 12 nm or less by forming micelle with polymeric lipid DSPE-mPEG having a molecular weight of 1500 to 2500 to encapsulate hyperricin which is a photosensitizer. Thus the nanopreparation easily overcomes a blood-tumor barrier (BTB) and an interstitial fluid pressure, as well as has light induced cytotoxicity efficiency that is about more than 2.5 times higher than that of the case where hypericin is used alone. Further, since a relative coexistence coefficient to a mitochondrion among intracellular organelles of cancer cells is high, the nanopreparation can be availably used to perform photodynamic diagnosis or treatment of cancer diseases, particularly brain tumors.

BRIEF DESCRIPTION OF THE DRAWINGS

The above and other objects, features and other advantages of the present invention will be more clearly understood from the following detailed description taken in conjunction with the accompanying drawings, in which:

FIG. 2B is a graph showing a size of the nanopreparation, a drug loading, binding efficiency, and cost efficiency of a preparation depending on a mixing molar ratio of hypericin, which is a photosensitizer, and DSPE-mPEG).

FIG. 3B is a graph showing a change in a size of the nanopreparation according to Example 2; FIG. 3C is a graph showing a change in a size of the nanopreparation according to Example 3; and FIG. 3D is a graph statistically showing sizes of the nanopreparations of Examples 1 to 3).

FIG. 4 is an image obtained by photographing the nanopreparation prepared in Example 1 through a transmission electron microscopy and a graph showing a size of the nanopreparation derived from the image (wherein, FIG. 4A shows an image obtained by negative staining the nanopreparation with sodium phosphotungstate and then photographing; and FIG. 4B shows an image obtained by photographing the nanopreparation without staining).

FIG. 6B is a graph showing light induced cytotoxicity efficiency to cancer cells when light is irradiated).

DESCRIPTION OF THE PREFERRED EMBODIMENTS

Figure 1:
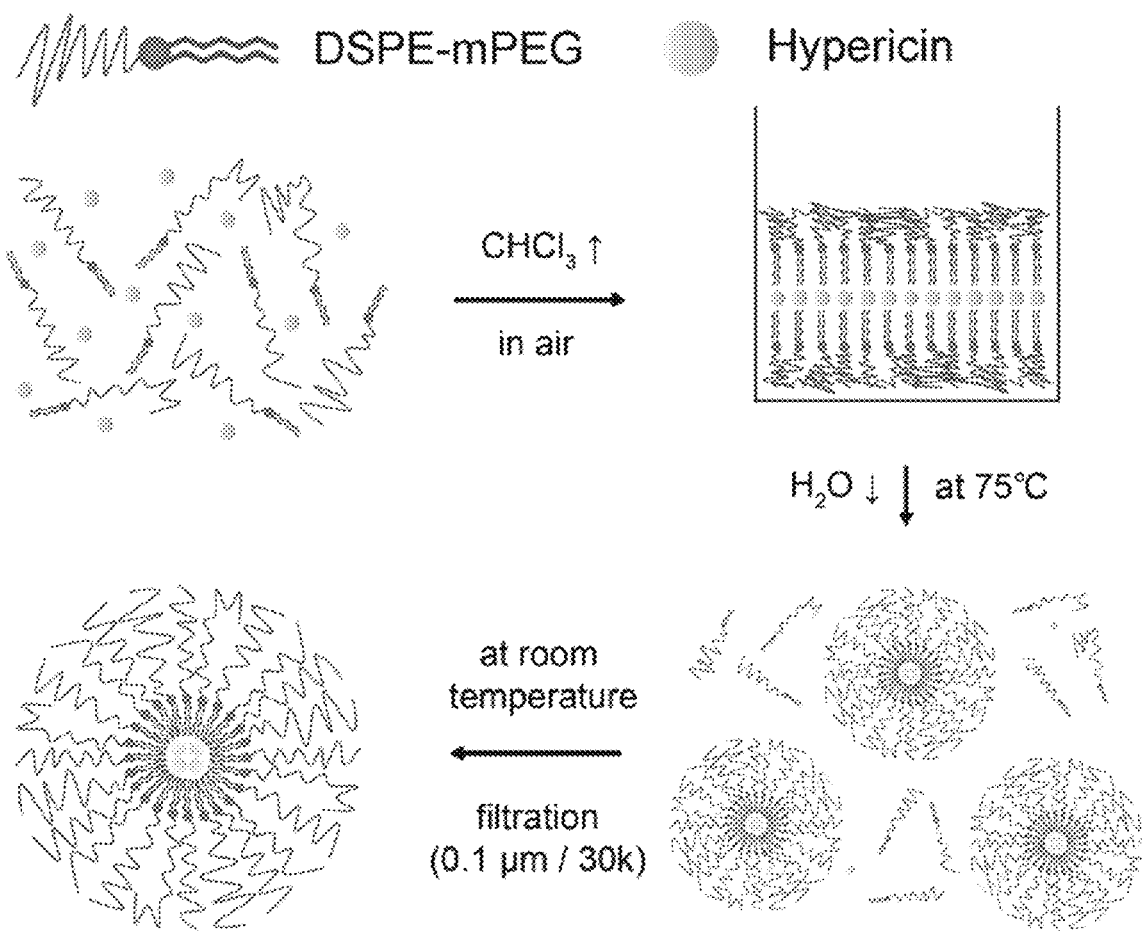
FIG. 1 shows a method of preparing a nanopreparation having a micelle structure according to the present invention.

Features and advantages of the present invention will be more clearly understood by the following detailed description of the present preferred embodiments by reference to the accompanying drawings. It is first noted that terms or words used herein should be construed as meanings or concepts corresponding with the technical sprit of the present invention, based on the principle that the inventor can appropriately define the concepts of the terms to best describe his own invention. Also, it should be understood that detailed descriptions of well-known functions and structures related to the present invention will be omitted so as not to unnecessarily obscure the important point of the present invention.

Hereinafter, the present invention will be described in detail.

The present invention provides a nanopreparation having a micelle structure for diagnosis or treatment of cancer diseases, the nanopreparation including:

1.0 molar ratio of a photosensitizer; and
5.0 to 15.0 molar ratios of polymeric lipid DSPE-mPEG.

In the nanopreparation having the micelle structure according to the present invention, it is preferable that the polymeric lipid DSPE-mPEGhas the molar ratio of 5.0 to 15.0 based on the total molar ratio of the nanopreparation.

When the molar ratio of DSPE-mPEG is less than 5.0, there are problems in that: incorporation efficiency of the nanopreparation is significantly deteriorated; a preparation cost increases; and resultangly, an encapsulation ratio of a drug is reduced. When the molar ratio is more than 15.0, it is problematic in that an amount of a photosensitizer included in the nanopreparation is not enough to reach an effective amount to thereby deteriorate drug efficiency due to problems such as a reduction in incorporation efficiency, a significant reduction in drug loading, an increase in a size of a nanodrug, and a significant increase in preparation cost, and thus the nanopreparation is not effective in use for diagnosis or treatment of cancer disease as well as in terms of preparation efficiency of a drug (see FIG. 3B).

Preferably, hypericin, expressed by following Formula 1, is used as a photosensitizer according to the present invention.

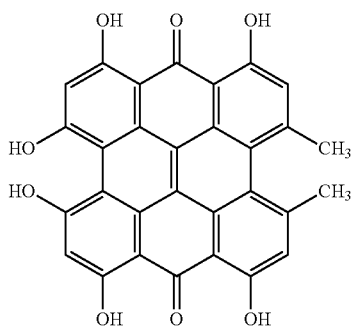

[Formula 1]

Hypericin is a natural pigment derived from a plant of genus *Hypericum*. When dissolved in ethanol, hypericin has a photosensitization effect exhibiting a maximum absorbance value at two wavelengths of 548 nm and 591 nm, and a maximum fluorescence emission at two wavelengths of 594 nm and 642 nm. Further, hypericin can be used as a strong selective inhibitor of protein kinase C, and has various pharmacological characteristics ranging from antibacterial activity or antiviral activity to antineoplastic activity and apoptosis inducement. Since, it is known that proteins or cells are not generally affected by a certain or less concentration of hypericin alone, and the aforementioned action of damaging proteins and cells occurs only when light is irradiated, the effects such as antineoplastic activity and apoptosis inducement have been used to diagnose or treat various cancer diseases (see Experimental Examples 3 and 4).

The polymeric lipid DSPE-mPEG according to the present invention has a molecular weight of 1500 to 2500.

When the molecular weight of the DSPE-mPEG according to the present invention falls out of the range of 1500 to 2500, it is difficult to use the nanopreparation to diagnose or treatment of cancer diseases, particularly a brain tumor due to a significant increase in a size of the prepared nanopreparation having the micelle structure or a significant reduction in drug preparation efficiency such as incorporation efficiency and a drug loading.

The nanopreparation according to the present invention has a size of 5.0 to 12.0 nm.

Figure 3:
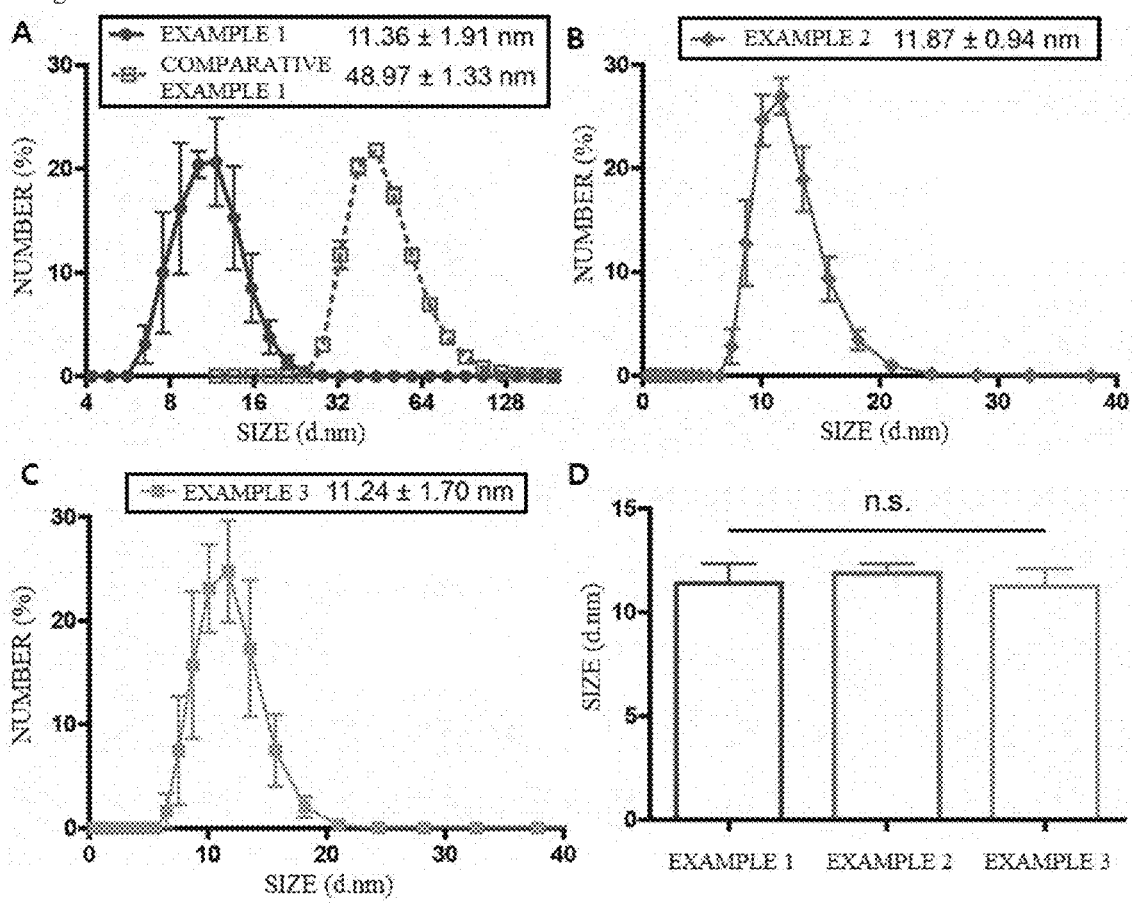
FIG. 3 is a graph showing a result obtained by measuring dynamic light scattering of nanopreparations having a micelle structure prepared in Examples 1 to 3 and Comparative Example 1 (wherein, FIG. 3A is a graph showing a change in a size of the nanopreparations according to Example 1 and Comparative Example 1.

As a result of measuring dynamic light scattering and photographing through transmission electron microscopy to evaluate a size of the nanopreparation having the micelle structure according to the present invention, it can be found that the size of the nanopreparation according to the present invention is distributed in the range of about 5 to 20 nm, particularly the size thereof is mostly distributed in the range of 9 to 12 nm (see Experimental Example 1 and FIG. 3).

Figure 5:
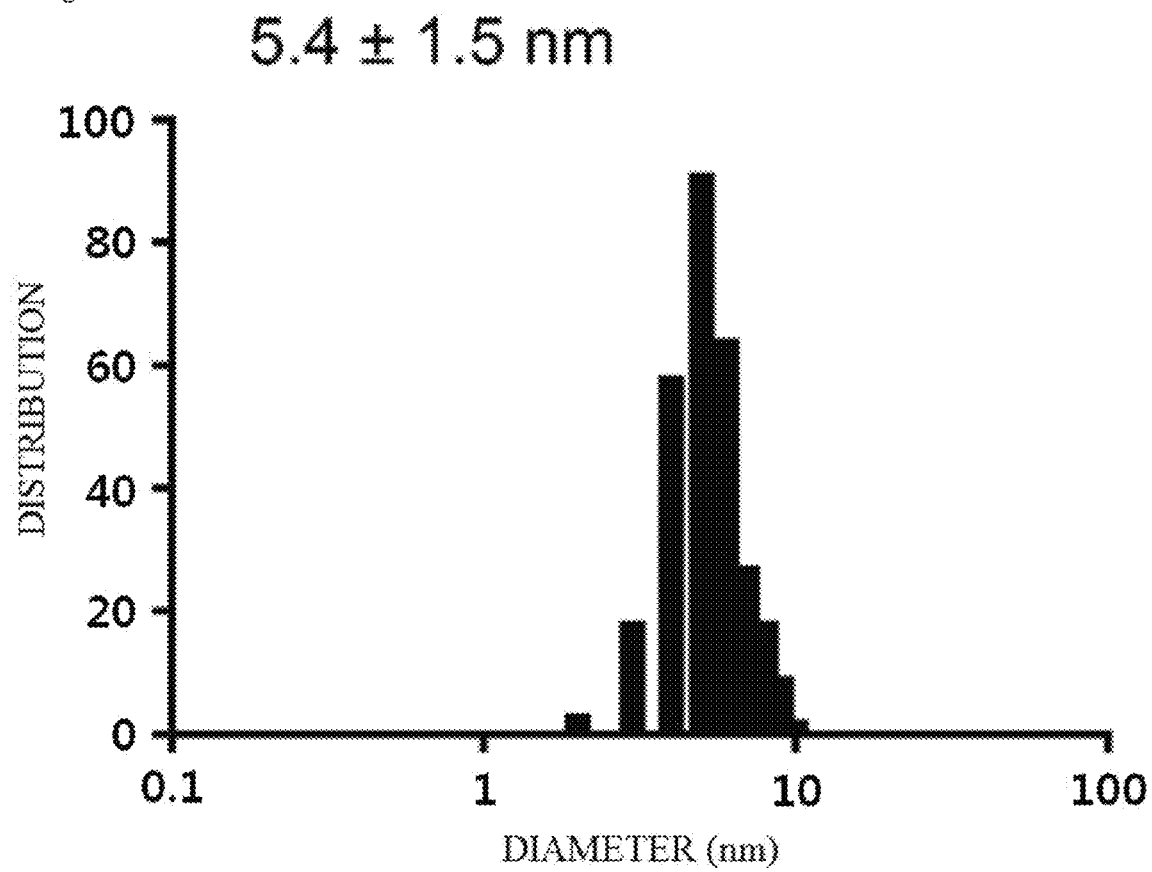
FIG. 5 is a graph showing a size of the nanopreparation derived from FIG. 4B which photographs the nanopreparation without staining through a transmission electron microscopy.

Further, from the result obtained by transmission electron microscopy, it can be found that the size of the nanopreparation is uniformly 11.1±3.5 nm when the nanopreparation is negatively stained with sodium phosphotungstate, and the size is uniformly 5.4±1.5 nm when the nanopreparation is not stained (see Experimental Example 2 and FIGS. 4 and 5).

Accordingly, it can be found that the size of the nanopreparation according to the present invention is 5.4±1.5 nm to 11.1±3.5 nm, that is, 5.0 to 12.0 nm.

Further, the nanopreparation according to the present invention is accumulated in a mitochondrion among intracellular organelles.

A relative coexistence coefficient of the nanopreparation according to the present invention between the intracellular organelles was measured. As a result, it was confirmed that the relative coexistence coefficient of drugs existing in the mitochondrion was 1.14 to 1.17 times higher than that of the case where anticancer substance hypericin was used alone or encapsulated with PEG (see Experimental Example 4).

A mitochondrion exists in a cell, and takes a role in ATP synthesis, which is an energy source, through ingested foods and plays a key role in respiration control. Further, the mitochondrion plays a role in killing defunctionalized cells, which is called "cellular suicide" or "apoptosis".

Cell shrinkage is accompanied by the "apoptosis". Subsequently, a gap is formed between the adjacent cells, and DNA is regularly cut and subjected to fragmentation within the cell, and thereby the cell is killed. Finally, the entire cell is subjected to fragmentation to be converted into an "apoptotic body", and then eaten by a neighborhood cell. As a result, the cell is killed. The "apoptosis" is in charge of forming a body's configuration during a development process, and renewing normal cells or removing abnormal cells in an adult. This "apoptosis" phenomenon occurs by a command of mitochondria.

Accordingly, the nanopreparation according to the present invention has an advantageous in that the nanopreparation is accumulated in a mitochondrion among intracellular organelles at a high content, thereby excellently inducing the apoptosis, i.e cell death of cancer cells.

Examples of the cancer disease according to the present invention may include, for example, colon cancer, liver cancer, gastric cancer, breast cancer, colorectal cancer, bone tumor and cancer, pancreatic cancer, head and neck tumors or cancers, uterine cancer, ovarian cancer, rectal cancer, esophageal cancer, small intestine cancer, perianal cancer, colorectal cancer, fallopian tube carcinoma, endometrial carcinoma, cervical carcinoma, vagina carcinoma, vulva carcinoma, Hodgkin's disease, prostate cancer, bladder cancer, renal cancer, ureter cancer, renal cell carcinoma, renal pelvis carcinoma, central nervous system tumors and cancers, and brain tumors.

In this case, examples of the brain tumors may include, but are not limited thereto, a pituitary tumor, meningioma, medulloblastoma, schwannoma, glioma, high-grade astrocytoma, glioblastoma, metastatic brain tumors, and other primary brain tumors.

Further, the present invention provides a method of preparing a nanopreparation having a micelle structure, the method including:

mixing polymeric lipid DSPE-mPEG and a photosensitizer dissolved in an organic solvent at a molar ratio of 1.0:5.0 to 15.0 to prepare a mixed solution (step 1);

removing the organic solvent from the mixed solution prepared in the step 1 and drying the resultant to prepare a polymeric lipid film (step 2);

hydrating the polymeric lipid film prepared in the step 2 in one or more solutions selected from the group consisting of water, PBS, HBS, and HBG at room temperature to 100° C. to form nanoparticles having the micelle structure (step 3); and filtering the nanoparticles having the micelle structure formed in the step 3 to homogenize (step 4).

Hereinafter, the method of preparing the nanopreparation having the micelle structure will be described in detail for each step.

Firstly, during step 1 according to the present invention, the photosensitizer and polymeric lipid DSPE-mPEG dissolved in an organic solvent are mixed at a molar ratio of 1.0:5.0 to 15.0 at room temperature under a dark room condition to prepare a mixed solution.

In this case, examples of the organic solvent of the step 1 according to the present invention may include, for example, chloroform, dimethyl sulfoxide, dimethylformamide, ethanol, methanol, tetrahydrofuran, toluene, xylene, and hexane, and preferably, chloroform may be used.

Further, it is preferable that polymeric lipid DSPE-mPEG of the step 1 according to the present invention has a molecular weight of 1500 to 2500. When the molecular weight of DSPE-mPEG falls out of a range of 1500 to 2500, a size of the prepared nanopreparation having the micelle structure significantly increases, and thereby cause a problem in that it is difficult to diagnose or treat cancer diseases, particularly brain tumors.

Preferably, hypericin, expressed by following Formula 1, is used as a photosensitizer according to the present invention.

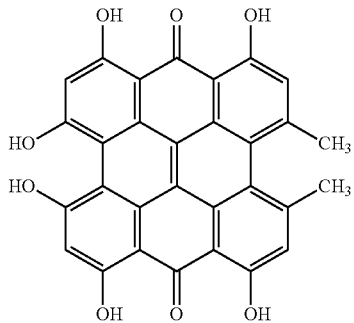

[Formula 1]

The hypericin is a natural pigment derived from a plant of genus *Hypericum*. when hypericin is dissolved in ethanol, hypericin has a photosensitization effect exhibiting a maximum absorbance value at wavelengths of 548 nm and 591 nm and a maximum fluorescence emission at wavelengths of 594 nm and 642 nm. Further, hypericin can be used as a strong selective inhibitor of protein kinase C, and has various pharmacological characteristics ranging from antibacterial activity or antiviral activity to antineoplastic activity and apoptosis inducement. Since, it is known that proteins or cells are not generally affected by a certain or less concentration of hypericin alone, and the aforementioned action of damaging proteins and cells occurs only when light is irradiated, the effects such as antineoplastic activity and apoptosis inducement have been used to diagnose or treat various cancer diseases (see Experimental Examples 3 and 4).

Next, during the step 2 according to the present invention, the organic solvent is removed from the mixed solution prepared in the step 1 and dried the resultant to prepare the polymeric lipid film. More specifically the resultant was completely dried under a room temperature-dark room condition to prepare a film in which the photosensitizer and polymeric lipid DSPE-mPEG are mixed with each other.

In this case, the film may be prepared by a film preparation method typically used in the art.

Next, during the step 3 according to the present invention, the polymeric lipid film prepared in the step 2 is hydrated in one or more solutions selected from the group consisting of water, PBS, HBS, and HBG at room temperature to 100° C. to form the nanoparticles having the micelle structure.

In this case, it is preferable that one or more solutions selected from the group consisting of PBS (phosphate buffered saline), HBS (HEPES buffered saline), and HBG (HEPES buffered glucose), which allows the polymeric lipid film prepared in the step 2 to be hydrated, is (are) used alone or in combination with each other as the solution of the step 3 according to the present invention.

Further, the hydrating of the step 3 may be performed in water, and aging may be then performed in one or more solutions selected from the group consisting of PBS, HBS, and HBG, or the hydrating of the step may be directly performed in one or more solutions selected from the group consisting of PBS, HBS, and HBG. In this case, a hydration time or an aging time is not particularly limited, but preferably 1 hour to overnight.

Moreover, the hydrating of the step 3 according to the present invention is performed by a sonicator. The hydrating and sonication may be performed simultaneously. The sonication more uniformly reduces a size of the micelle produced by the hydrating.

Next, during the step 4 according to the present invention, the nanoparticles having the micelle structure formed in the step 3 are filtered to be homogenized.

In this case, the filtering of the step 4 according to the present invention may be performed by a method including:

filtering the nanoparticles having the micelle structure formed in the step 3 by a filter of 0.05 to 0.20 μm (step A); and re-filtering the nanoparticles filtered in the step A by a centrifugal filter of 20 to 40 K (step B).

Hereinafter, the present invention will be described in more detail with reference to the following Examples, Comparative Examples, and Experimental Examples.

However, the following Examples and Experimental Examples are provided for speicifically illustrative the present invention, and the scope of the present invention should not be limited thereto in any manner.

<Setting of Preparation Condition of Nanopreparation Having Micelle Structure>

To investigate an optimal condition for preparation of the nanopreparation having the micelle structure according to the present invention, the following procedure was performed.

1. Optimal Molecular Weight of Polymeric Lipid

Figure 2:
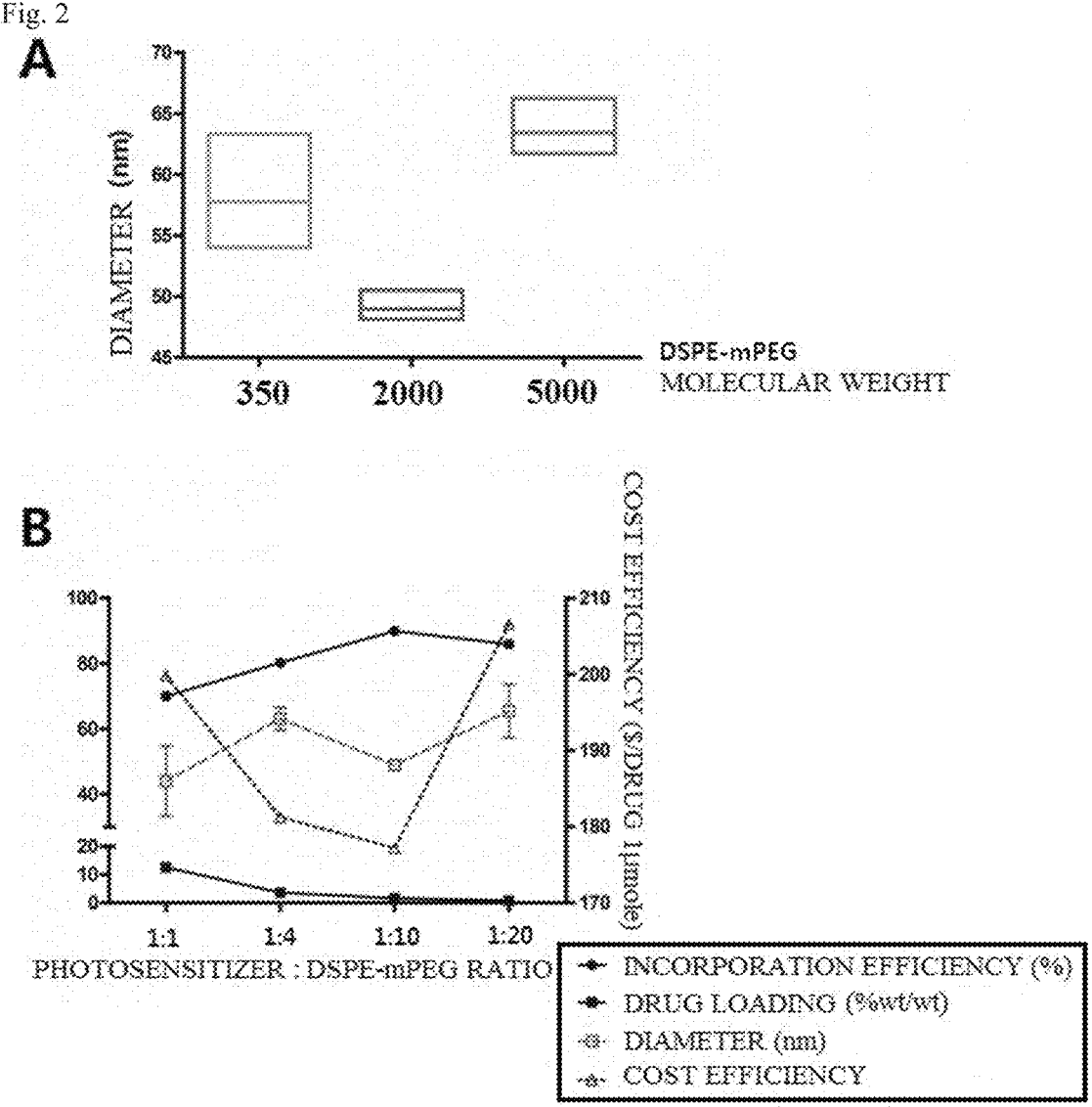
FIG. 2 is a graph showing a result obtained by measuring dynamic light scattering of an optimal condition of the nanopreparation according to the present invention (wherein FIG. 2A is a graph showing a change in a size of the nanopreparation depending on a molecular weight of DSPE-mPEG.

To investigate a change in a size of a nanopreparation depending on molecular weights of polymeric lipid DSPE-mPEG which encapsulates hypericin that is a photosensitizer, DSPE-mPEGs having the molecular weights of 350, 2000, and 5000 were respectively mixed with hypericin, which is a photosensitizer, at room temperature. The molar ratio of hypericin and DSPE-mPEG was 1:10. Subsequently, the resulting mixture was completely dried in a room temperature-light blocking state to form a polymeric lipid film, and the formed film was introduced into sonication equipment together with water (1 mL) at 75° C., and hydrated in an ultrasonic water bath for 5 minutes. After the hydrated solution was cooled to room temperature and filtered by a filter having the size of 0.1 μm, the filtrate was further filtered by centrifuge with a 30 k centrifugal filter (30000 MWCO centrifuge, Millipore, Billerica, Mass., USA) to prepare a nanopreparation having a micelle structure. Next, the prepared nanopreparation was aged in water and then evaluated at 25° C. Subsequently, dynamic light scattering measurement of the hydrodynamic size, polydispersity (PI), and the zeta potential of the nanopreparation was performed by zetasizer Nano ZS90 (Malvern Instrument Ltds., Worcestershire, UK). The result is shown in FIG. 2A.

As shown in FIG. 2A, it was confirmed that when the molecular weights of polymeric lipid DSPE-mPEG were 350 and 5000, the measured diameters were about 54 to 63 nm and about 61 to 66 nm, respectively; however it could be found that when the molecular weight of DSPE-mPEG was 2000, the diameter was about 48 to 50 nm which means the size of the nanopreparation was reduced by about 11.1 to 24.2%.

Accordingly, it was found that the optimal molecular weight of polymeric lipid DSPE-mPEG, which may be used to prepare the nanopreparation having the micelle structure, was 1500 to 2500.

2. Optimal Molar Ratio of Photosensitizer and Polymeric Lipid

To investigate a change in a size of a nanopreparation depending on a molar ratio of hypericin, which is a photosensitizer, and polymeric lipid DSPE-mPEG, hypericin, and DSPE-mPEG having the molecular weight of 2000 were mixed at room temperature to have the molar ratio of 1:1, 1:4, 1:10, and 1:20. Subsequently, the resulting mixture was completely dried in a room temperature-light blocking state to form a polymeric lipid film, and the formed film was introduced into sonication equipment together with water (1 mL) at 75° C., and hydrated in an ultrasonic water bath for 5 minutes. After the hydrated solution was cooled to room temperature and filtered by a filter having the size of 0.1 μm, the filtrate was further filtered by centrifuge with a 30 k centrifugal filter (30000 MWCO centrifuge, Millipore, Billerica, Mass., USA) to prepare a nanopreparation having a micelle structure. Next, the prepared nanopreparation was aged in water and then evaluated at 25° C. Subsequently, dynamic light scattering measurement of the hydrodynamic size, polydispersity (PI), and the zeta potential of the nanopreparation was performed by zetasizer Nano ZS90 (Malvern Instrument Ltds., Worcestershire, UK). The result is shown in B of FIG. 2.

As shown in FIG. 2B, in review of physical properties such as binding force between components of the nanopreparation depending on the mixing ratio of hypericin, which is a photosensitizer, and polymeric lipid DSPE-mPEG, it can be found that when the molar ratio of DSPE-mPEG is 1 or 4 based on 1 mole of hypericin, binding efficiency of hypericin, which is a photosensitizer, and DSPE-mPEG is reduced, and also preparation cost increases due to an increase in an amount of hypericin used as an active ingredient. Further, it can be found that when the molar ratio of DSPE-mPEG is 20 based on 1 mole of hypericin, the amount of the photosensitizer included in the nanopreparation is not enough to reach an effective amount to thereby deteriorate drug efficiency due to problems such as a reduction in incorporation efficiency, a significant reduction in a drug loading, an increase in a size of a nanodrug, and a significant increase in preparation cost.

On the contrary, it can be found that when the molar ratio of DSPE-mPEG is 10 based on 1 mole of hypericin, binding efficiency with hypericin is about 89.9%, which is very high, and the preparation cost is significantly reduced.

Accordingly, it was found that the optimal molar ratio of the photosensitizer and the polymeric lipid used to prepare the nanopreparation having the micelle structure is 1:5 to 15.

Example 1

Preparation of Nanopreparation Having Micelle Structure According to Present Invention 1

Hypericin (200 μL, 0.2 mg/mL) and DSPE-mPEG (1,2-distearoyl-sn-glycero-3-phosphoethanolamine-N-[methoxy-poly(ethylene glycol), molecular weight 2000], 222 μL, 10 mg/mL) dissolved in chloroform were mixed at room temperature to have a molar ratio of 1:10. Subsequently, the resulting mixture was completely dried in a room temperature-light blocking state to form a polymeric lipid film, and the formed film was introduced into sonication equipment, and then hydrated in phosphate buffered saline (PBS, 1 mL) at 75° C. for 5 minutes. In this case, the polymeric lipid film was hydrated and sonicated simultaneously. After the sonicated solution was cooled to room temperature and filtered by a filter having the size of 0.1 μm, the filtrate was further filtered by centrifuge with a 30 k centrifugal filter (30000 MWCO centrifuge, Millipore, Billerica, Mass., USA) to prepare a nanopreparation having a micelle structure.

The phosphate buffered saline (PBS) includes water; 10 to 20 mM of sodium phosphate; and 0.9% of sodium chloride.

Example 2

Preparation of Nanopreparation Having Micelle Structure According to Present Invention 2

The same procedure as Example 1 was performed to prepare a nanopreparation having a micelle structure, except that HEPES buffered saline (HBS, 1 mL) was used instead of phosphate buffered saline (PBS, 1 mL) used in the Example 1.

The HEPES buffered saline (HBS) includes water; 10 to 20 mM 4-(2-hydroxyethyl)piperazine-1-ethanesulfonic acid; and 135 to 155 mM sodium chloride.

Example 3

Preparation of Nanopreparation Having Micelle Structure According to Present Invention 3

The same procedure as Example 1 was performed to prepare a nanopreparation having a micelle structure, except that HEPES buffered glucose solution (HBG, 1 mL) was used instead of phosphate buffered saline (PBS, 1 mL) used in Example 1.

The HEPES buffered glucose solution (HBG) includes water; 10 to 20 mM 4-(2-hydroxyethyl)piperazine-1-ethanesulfonic acid; and 5% of glucose.

Example 4

Preparation of Nanopreparation Having Micelle Structure According to Present Invention 4

Hypericin (200 μL, 0.2 mg/mL) and DSPE-mPEG (1,2-distearoyl-sn-glycero-3-phosphoethanolamine-N-[methoxy-poly(ethylene glycol), molecular weight 2000], 222 μL, 10 mg/mL) dissolved in chloroform were mixed at room temperature to have a molar ratio of 1:10.

Next, the resulting mixture was completely dried in a room temperature-light blocking state to form a polymeric lipid film, and the formed film was introduced into sonication equipment, and then hydrated in water (1 mL) at 75° C. for 5 minutes. In this case, the polymeric lipid film was hydrated and sonicated simultaneously. After the sonicated solution was cooled to room temperature and filtered by a filter having the size of 0.1 μm, the filtrate was further filtered by centrifuge with a 30 k centrifugal filter (30000 MWCO centrifuge, Millipore, Billerica, Mass., USA).

Next, the prepared nanopreparation was aged overnight in phosphate buffered saline (PBS) to prepare a nanopreparation having a micelle structure.

Example 5

Preparation of Nanopreparation Having Micelle Structure According to Present Invention 5

The same procedure as Example 4 was performed to prepare a nanopreparation having a micelle structure, except that aging was performed overnight in HEPES buffered saline (HBS) instead of phosphate buffered saline (PBS) in Example 4.

Example 6

Preparation of Nanopreparation Having Micelle Structure According to Present Invention 6

The same procedure as Example 4 was performed to prepare a nanopreparation having a micelle structure, except that aging was performed overnight in HEPES buffered glucose solution (HBG) instead of phosphate buffered saline (PBS) in Example 4.

Comparative Example 1

Preparation of Nanopreparation Having Micelle Structure Hydrated and Aged in Water Hypericin (200 µL, 0.2 mg/mL) and DSPE-mPEG (1,2-distearoyl-sn-glycero-3-phosphoethanolamine-N-[methoxy-poly(ethylene glycol), molecular weight 2000], 222 µL, 10 mg/mL) dissolved in chloroform were mixed at room temperature to have a molar ratio of 1:10.

Next, the resulting mixture was completely dried in a room temperature-light blocking state to form a polymeric lipid film, and the formed film was introduced into sonication equipment and then hydrated in water (1 mL) at 75° C. for 5 minutes. In this case, the polymeric lipid film was hydrated and sonicated simultaneously. After the sonicated solution was cooled to room temperature and filtered by a filter having the size of 0.1 µm, the filtrate was further filtered by centrifuge with a 30 k centrifugal filter (30000 MWCO centrifuge, Millipore, Billerica, Mass., USA) to prepare a nanopreparation having a micelle structure.

Comparative Example 2

Preparation of Nanopreparation Including Photosensitizer

Hypericin, which is a photosensitizer, was dissolved in dimethyl sulfoxide (DMSO) to adjust to 16 mg/mL. Subsequently, before the cell was treated with hypericin completely dissolved in dimethyl sulfoxide in a room temperature-light blocking state, hypericin was mixed with a cell culture medium to adjust volume of dimethyl sulfoxide to 1 vol % or less. Then, cell treatment was performed.

Comparative Example 3

Nanopreparation Having Micelle Structure Depending on Organic Solvent

The same procedure as Example 1 was performed to prepare a nanopreparation having a micelle structure, except that hypericin (62.5 µL, 31.72 mM) and DSPE-mPEG (molecular weight 400, 62.5 µL, 31.72 mM) respectively dissolved in the same volume of dimethyl sulfoxide (DMSO) were mixed instead of hypericin (200 µL, 0.2 mg/mL) and DSPE-mPEG (molecular weight 2000, 222 µL, 10 mg/mL) in Example 1 which were dissolved in chloroform and mixed at room temperature to have a molar ratio of 1:10.

Experimental Example 1

Evaluation of Size and Physical Properties of Nanopreparation Having Micelle Structure 1

The following experiment was performed to evaluate a size of the nanopreparation having the micelle structure prepared according to the present invention.

Firstly, the nanopreparations having the micelle structure prepared in Examples 1 to 3 by directly hydrating in phosphate buffered saline (PBS), HEPES buffered saline (HBS), or the HEPES buffered glucose solution (HBG) were respecvely aged overnight in water, phosphate buffered saline (PBS), HEPES buffered saline (HBS), or the HEPES buffered glucose solution (HBG), or the nanopreparations having the micelle structure prepared in Examples 1 to 3 by directly hydrating in phosphate buffered saline (PBS), HEPES buffered saline (HBS), and the HEPES buffered glucose solution (HBG) were not subjected to aging. Then, the aged or non-aged nanopreparations were evaluated at 25° C. Subsequently, the non-aged or aged nanopreparation solutions were diluted 10 to 20 folds, and dynamic light scattering measurement of the hydrodynamic size, polydispersity (PI), and the zeta potential of the nanopreparations was performed by zetasizer Nano ZS90 (Malvern Instrument Ltds., Worcestershire, UK). The result is shown in FIG. 3.

As shown in FIG. 3, from the result obtained by measuring dynamic light scattering of the nanopreparations prepared in Examples 1 to 3 according to the present invention, it can be found that the sizes of the nanopreparations are distributed in the range of about 5 to 20 nm, and particularly mostly distributed in the range of about 9 to 12 nm.

Accordingly, it can be found that the nanopreparations prepared by forming the micelle using polymeric lipid DSPE-mPEG and hypericin, which is a photosensitizer, according to the present invention have the size of about 12 nm or less.

Therefore, according to the present invention, the nanopreparation having the micelle structure having the size of 12 nm or less due to high binding efficiency of hypericin and DSPE-mPEG can be economically prepared by: encapsulating hypericin, which is a photosensitizer, and polymeric lipid DSPE-mPEG having the molecular weight of 1500 to 2500 which are used at a ratio of 1:5.0 to 15.0; and hydrating the resultant in water, and then aging in phosphate buffered saline (PBS), HEPES buffered saline (HBS), or the HEPES buffered glucose solution (HBG); or directly hydrating the resultant in phosphate buffered saline (PBS), HEPES buffered saline (HBS), or the HEPES buffered glucose solution (HBG). Therefore, the nanopreparation having the micelle structure according to the present invention may be availably used to diagnose or treat cancer diseases such as colon cancer, liver cancer, gastric cancer, breast cancer, colorectal cancer, bone tumor and cancer, pancreatic cancer, head and neck tumors or cancers, uterine cancer, ovarian cancer, rectal cancer, esophageal cancer, small intestine cancer, perianal cancer, colorectal cancer, fallopian tube carcinoma, endometrial carcinoma, cervical carcinoma, vagina carcinoma, vulva carcinoma, Hodgkin's disease, prostate cancer, bladder cancer, renal cancer, ureter cancer, renal cell carcinoma, renal pelvis carcinoma, central nervous system tumors and cancers, and particularly the brain tumors.

Experimental Example 2

Evaluation of Size of Nanopreparation Having Micelle Structure 2

The following experiment was performed to evaluate a size of the nanopreparation having the micelle structure prepared according to the present invention.

One drop of the nanopreparation prepared in Example 1 was dripped on a carbon support film in which the 400 mesh copper grid (Ted Pella Inc., Pedding, Ca, USA) was supported, and completely dried the resultant to form a film. Then, the formed film was photographed by a transmission electron microscopy (TEM, JEM-2100F, JEOP Ltd., Tokyo, Japan) at 200 kV. The result is shown in FIGS. 4 to 5. The photographing was performed on an unstained nanopreparation film and a stained nanopreparation film. In this case, the stained nanopreparation film was prepared by: treating the formed film with 1% sodium phosphotungstate (PTA, Sigma-Aldrich) aqueous solution having the pH adjusted to 7.2 to 7.4 with 0.1 N NaOH; and drying the film on a Petri dish for 15 to 20 minutes.

As shown in FIGS. 4 to 5, it can be found that the nanopreparation having the micelle structure according to the present invention has the size of 3.0 to 14.5 nm.

To be more specific, from the result obtained by photographing the nanopreparation prepared in Example 1 according to the present invention through a transmission electron microscopy, it can be found that when the nanopreparation is stained with sodium phosphotungstate, the size of the nanopreparation is uniformly 11.1±3.5 nm (FIG. 4A). Further, it can be found that when the nanopreparation is not stained, the size is uniformly 5.4±1.5 nm (FIGS. 4B and 5).

Accordingly, it can be found that the size of the nanopreparation according to the present invention is 5.4±1.5 nm to 11.1±3.5 nm, that is, 5.0 to 12.0 nm.

Therefore, since the nanopreparation having the micelle structure according to the present invention has the size of 5.0 to 12.0 nm, the nanopreparation may be availably used to diagnose or treat cancer disease such as colon cancer, liver cancer, gastric cancer, breast cancer, colorectal cancer, bone tumor and cancer, pancreatic cancer, head and neck tumors or cancers, uterine cancer, ovarian cancer, rectal cancer, esophageal cancer, small intestine cancer, perianal cancer, colorectal cancer, fallopian tube carcinoma, endometrial carcinoma, cervical carcinoma, vagina carcinoma, vulva carcinoma, Hodgkin's disease, prostate cancer, bladder cancer, renal cancer, ureter cancer, renal cell carcinoma, renal pelvis carcinoma, central nervous system tumors and cancers, and particularly the brain tumors.

Experimental Example 3

Evaluation of Cytotoxicity of Nanopreparation Having Micelle Structure

The following experiment was performed to evaluate cytotoxicity of the nanopreparation having the micelle structure according to the present invention when light is not irradiated.

In order to evaluate cytotoxicity, U251MG, which is a human malignant glioma cell, was obtained from American Type Culture Collection (ATCC, Manassas, Va., USA). The obtained cell was cultured in a Dulbecco's Modified Eagle's Medium including the nutrient mixture F-12, 10% fetal bovine serum, an antibiotic (penicillin (100 I.U./mL), and streptomycin (100 μg/mL)), and the 0.1 mM MEM non-essential amino acid solution under conditions of 37° C. and 5% carbon dioxide. $5 \times 10^4$ cell/well of the cultured cells were dispensed into a 24-well plate, and DMEM/F12 medium (1 mL) was injected four times for each sample. The medium was removed 24 hours after culture, and media respectively including nanopreparations prepared in Example 1 and Comparative Examples 2 and 3 in concentrations of 1.0, 2.5, 5.0, and 10 μM were injected. In this case, the volume of the nanopreparations included in the injected medium was set not to exceed 1.0% of the total volume of the medium. Two hours after the culture, each well was washed with a phosphate buffered solution (PBS) and a medium without the nanopreparation was injected to perform an additional culture for 24 hours. Subsequently, in order to evaluate cell viability and cytotoxicity, the medium of each well was treated with 10 vol % of WST-1 reagent (DAEILLAB SERVICE Co., Ltd., Seoul, Korea) and cultured for 1 hour. Then, absorbance of the culture medium was measured at the wavelength of 450 nm by using an absorbance microplate reader. In this case, the aforementioned whole procedure was performed at a dark room condition, and cell viability was derived from the measured normalized absorbance. The result is shown in FIG. 6A.

Figure 6:
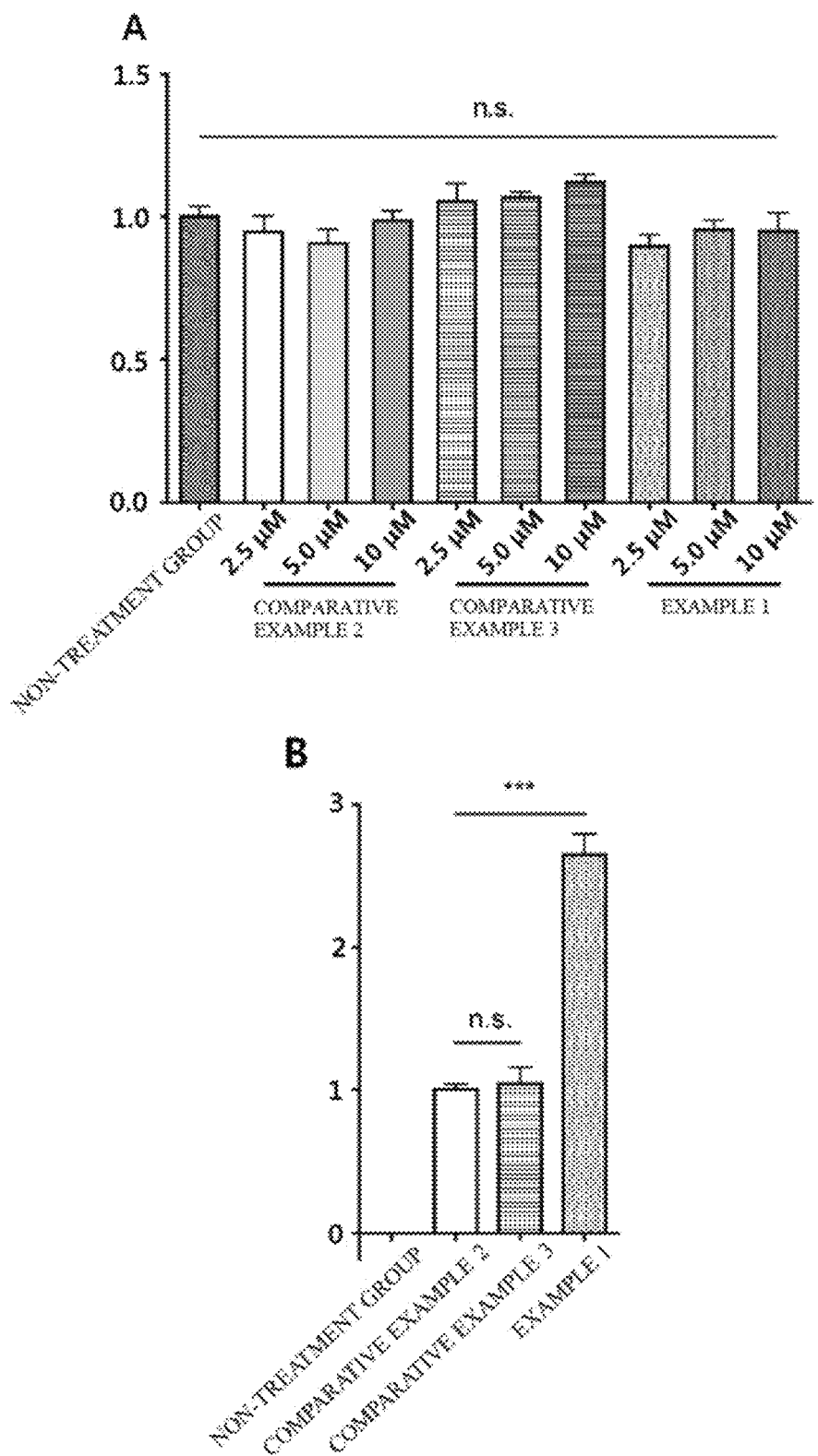
FIG. 6 is a graph showing cytotoxicity of the nanopreparations prepared in Example 1 and Comparative Examples 2 and 3 to U251MG which is a human malignant glioma cell (wherein, FIG. 6A is a graph showing cytotoxicity when light is not irradiated.

As shown in FIG. 6A, it can be found that the nanopreparation having the micelle structure according to the present invention does not have toxicity to cells. To be more specific, it can be found that 10 μM or less of concentration of nanopreparations prepared in Comparative Example 2 (including a photosensitizer hypericin alone), Comparative Example 3, or Example 1 (in which hypericin is encapsulated by forming a micelle with mPEG or DSPE-mPEG) do not have toxicity to cells under the dark room condition where light is not irradiated.

Therefore, the nanopreparation having the micelle structure according to the present invention does not have toxicity to cells when light is not irradiated, and is thus safe to a human body. Accordingly, the nanopreparation may be availably used to diagnose or treat cancer diseases such as colon cancer, liver cancer, gastric cancer, breast cancer, colorectal cancer, bone tumor and cancer, pancreatic cancer, head and neck tumors or cancers, uterine cancer, ovarian cancer, rectal cancer, esophageal cancer, small intestine cancer, perianal cancer, colorectal cancer, fallopian tube carcinoma, endometrial carcinoma, cervical carcinoma, vagina carcinoma, vulva carcinoma, Hodgkin's disease, prostate cancer, bladder cancer, renal cancer, ureter cancer, renal cell carcinoma, renal pelvis carcinoma, central nervous system tumors and cancers, and particularly the brain tumors.

Experimental Example 4

Evaluation of Light Induced Cytotoxicity of Nanopreparation by Light Irradiation The following experiment was performed to evaluate light induced cytotoxicity when light is irradiated to the nanopreparation having the micelle structure according to the present invention.

$1 \times 10^4$ cell/well of U251MG, which is a human malignant glioma cell, were dispensed into a 96-well plate, and a DMEM/F12 medium (100 μL) was injected four times for each sample. 24 hours after culture, the medium was replaced with media respectively including the nanopreparations prepared in Example 1 and Comparative Examples 2 and 3 (sample treatment group) and a medium without the nanopreparation (non-treatment group). The samples were cultured at the dark room condition for 2 hours, washed with phosphate buffered saline (PBS). Then, media was replaced again with media without the nanopreparation. Subsequently, 5 mW/cm² of lighting power of light (590 to 605 nm) was irradiated through a light irradiation system (LIS) so that total energy applied to each cell is adjusted to 0.1 J/cm² to perform photodynamic diagnosis (photodynamic therapy). Each cell was cultured for 12 hours at the light irradiation condition. The cultured cell was subjected to the same method as Experimental Example 3 to measure light-cytotoxicity. Light induced cytotoxicity and light induced cytotoxicity efficiency were derived from the measured values by using Equations 1 and 2. The result is shown in FIG. 6B.

$$\text{light induced cytotoxicity (\%)} = \left(1 - \frac{\text{measured value of absorbance of the sample treatment group } (A.U.)}{\text{measured value of absorbance of the non-treatment group } (A.U.)}\right) \times 100 \quad \text{[Equation 1]}$$

$$\text{light induced cytotoxicity efficiency (\% mg/}A.U.\text{ ml)} = \frac{\text{light induced cytotoxicity (\%)}}{\text{absorption of the sample by the cell}(A.U.\text{ ml/mg})} \quad \text{[Equation 2]}$$

As shown in FIG. 6B, it can be found that the nanopreparation having the micelle structure according to the present invention has excellent light induced cytotoxicity which kills cancer cells when light is irradiated.

To be more specific, it can be found that when U251MG, which is a human malignant glioma cell, was treated with the nanopreparation of Example 1 according to the present invention, light toxicity of 2.65±0.15% mg/A.U. mL is exhibited. On the contrary, when the nanopreparation of Comparative Example 2 including hypericin alone as the photosensitizer and the nanopreparation of Comparative Example 3 in which hypericin is encapsulated by forming micelle using mPEG were treated, light toxicity of 1.00±0.04% mg/A.U. mL and 1.0±0.12% mg/A.U. mL were respective exhibited. Thus, it can be found that light induced cytotoxicity of the preparations of Comparative Examples 2 and 3 is significantly lower as compared to that of the nanopreparation of Example 1. Accordingly, it can be found that the nanopreparation having the micelle structure according to the present invention has excellent light induced cytotoxicity that is 2.5 times higher than that of the nanopreparation including only hypericin as the photosensitizer or the nanopreparation in which the micelle is formed by the polymeric lipid such as mPEG to encapsulate.

Therefore, since the nanopreparation having the micelle structure according to the present invention has excellent light induced cytotoxicity to cancer cells when light is irradiated, the nanopreparation may be availably used to diagnose or treat cancer diseases such as colon cancer, liver cancer, gastric cancer, breast cancer, colorectal cancer, bone tumor and cancer, pancreatic cancer, head and neck tumors or cancers, uterine cancer, ovarian cancer, rectal cancer, esophageal cancer, small intestine cancer, perianal cancer, colorectal cancer, fallopian tube carcinoma, endometrial carcinoma, cervical carcinoma, vagina carcinoma, vulva carcinoma, Hodgkin's disease, prostate cancer, bladder cancer, renal cancer, ureter cancer, renal cell carcinoma, renal pelvis carcinoma, central nervous system tumors and cancers, and particularly the brain tumors.

Experimental Example 5

Evaluation of Distribution Pattern of Nanopreparation in the Intracellular Organelles The following experiment was performed to evaluate a distribution pattern in intracellular organelles when the nanopreparation having the micelle structure according to the present invention was absorbed into a cell.

3×10⁵ cell/well of U251MG, which is a human malignant glioma cell, was suspended into a 35 mm culture dish together with a DMEM/F12 medium (1 mL). 24 hours after culture, the cells were respectively treated with the nanopreparations (5 μM) of Example 1 and Comparative Examples 2 and 3, and cultured for 2 hours. Then, the samples were treated with the Mito Tracker® deep red FM (200 nM, cultured for 10 minutes after treatment), ER-Tracker™ green (1 μM, cultured for 30 minutes after treatment), and LysoTracker® Blue DND-22 (75 nM, cultured for 2 hours after treatment), the samples and the dyes were washed with phosphate buffered saline (PBS), and the medium were replaced into the samples. In this case, the aforementioned process was performed at the dark room condition. The fluorescent microscope photographying image of the cell was obtained by using the multiphoton laser scanning microscopy imaging system (LSM 510; Carl Zeiss), and the continuous wavelength lasers of 488, 543, and 633 nm and the femto-second pulsed laser of 800 mm were used as excited light. Further, the emission filters of 390 to 465, 530 to 550, 560 to 615, and 650 to 710 nm were used, and photographying was performed by using the open perfusion micro-incubator (PDMI-2; Harvard Apparatus, Holliston, Mass., USA) at conditions of 37° C. and 5% carbon dioxide. The photographed images and the relative coexistence coefficients of the intracellular organelles derived from the images are shown in FIGS. 7 and 8.

Figure 7:
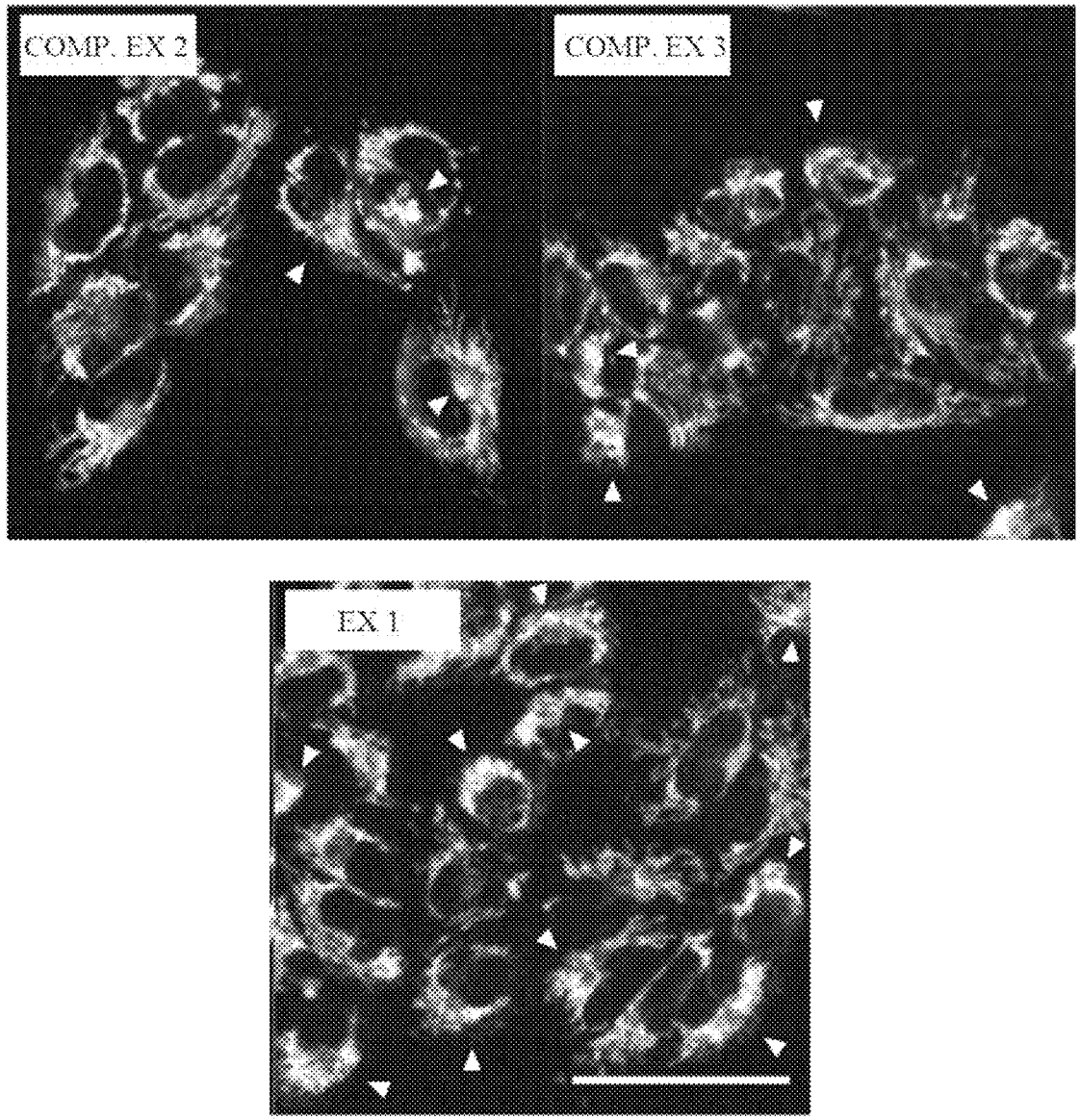
FIG. 7 is an image obtained by photographing mitochondria of cancer cells treated with the nanopreparations prepared in Example 1 and Comparative Examples 2 and 3 by confocal and multiphoton laser scanning microscope imaging system.
Figure 8:
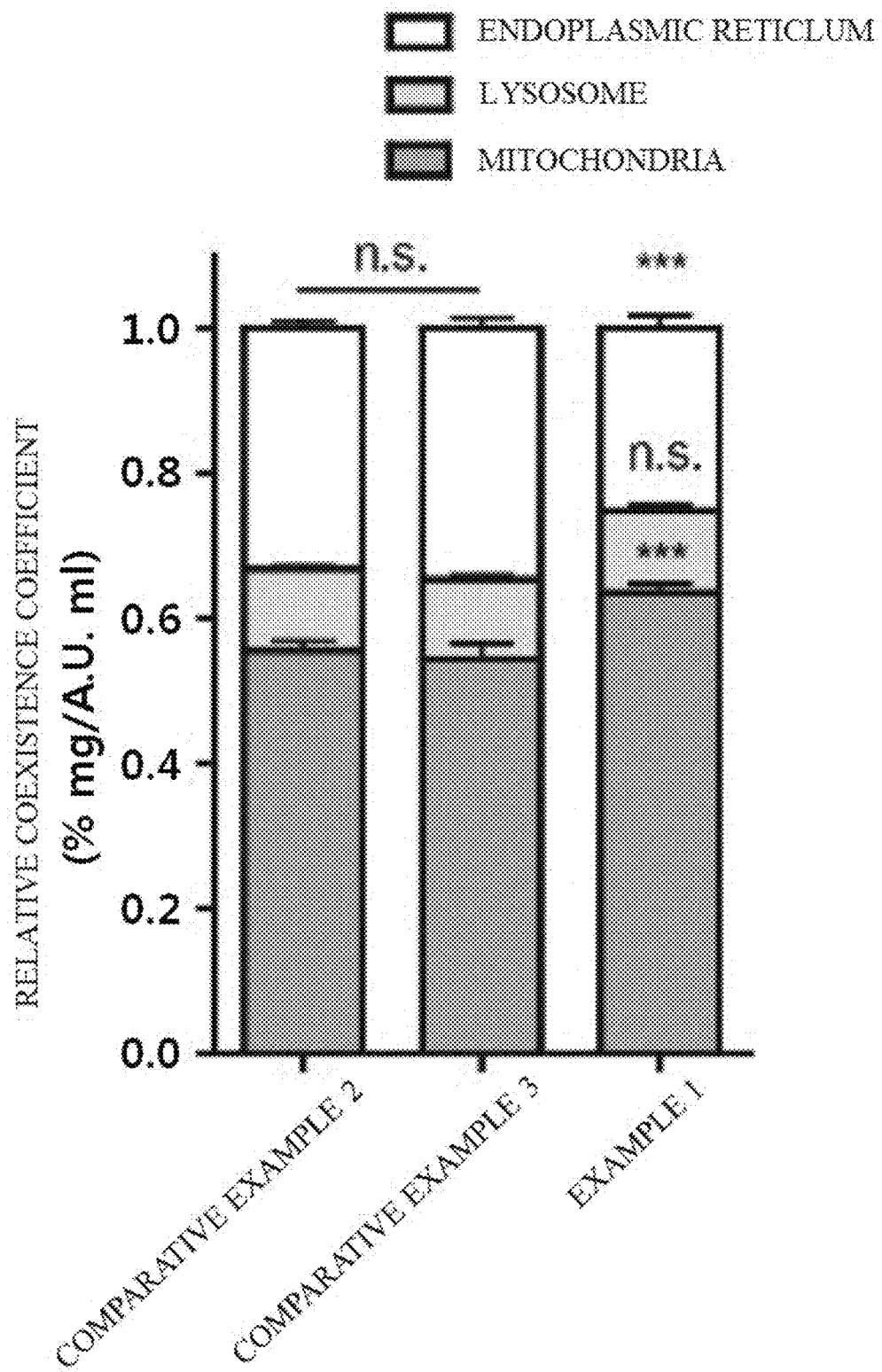
FIG. 8 is a graph showing a relative coexistence coefficient derived from the image photographed by using the confocal and multiphoton laser scanning microscope imaging system.

As shown in FIGS. 7 and 8, it can be found that the nanopreparation having the micelle structure according to the present invention is distributed at a high content in a mitochondrion among intracellular organelles, and thus light induced cytotoxicity efficiency is excellent.

To be more specific, from the photographed image of FIG. 7 which is pseudo-colored so that: the green denotes mitochondria; the red denotes hypericin; and the yellow indicated by an arrow denotes hypericin coexisting in mitochondria, it can be found that the nanopreparations of Example 1 according to the present invention are distributed in entire mitochondria, but the nanopreparations prepared in Comparative Examples 2 and 3 coexist only in a portion of mitochondria.

Further, from FIG. 8 showing the relative coexistence coefficient of the intracellular organelles based on the photographed image, it can be found that the nanopreparation of Comparative Example 2 including hypericin alone and the nanopreparation of Comparative Example 3, in which hypericin is encapsulated by forming micelle with mPEG, have the relative coexistence coefficients that are similar to each other; however, the nanopreparation of Example 1 according to the present invention has a relative coexistence coefficient of a mitochondrion that is higher than those of the nanopreparations of Comparative Examples 2 and 3.

Accordingly, from the relation of the nanopreparation having the micelle structure of the present invention to a period transfer mitochondrion of light induced cytotoxicity of hypericin, it can be found that the nanopreparation of the present invention has improved light induced cytotoxicity efficiency to cancer cells as compared to a known preparation including hypericin.

Therefore, the nanopreparations having the micelle structure according to the present invention are distributed at a high content in a mitochondrion among intracellular organelles to effectively exhibit light induced cytotoxicity to cancer cells. Accordingly, the nanopreparation may be availably used to diagnose or treat cancer diseases such as colon cancer, liver cancer, gastric cancer, breast cancer, colorectal cancer, bone tumor and cancer, pancreatic cancer, head and neck tumors or cancers, uterine cancer, ovarian cancer, rectal cancer, esophageal cancer, small intestine cancer, perianal cancer, colorectal cancer, fallopian tube carcinoma, endometrial carcinoma, cervical carcinoma, vagina carcinoma, vulva carcinoma, Hodgkin's disease, prostate cancer, bladder cancer, renal cancer, ureter cancer, renal cell carcinoma, renal pelvis carcinoma, central nervous system tumors and cancers, and particularly the brain tumors.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method of preparing a nanopreparation having a micelle structure, comprising the following steps:
   (1) mixing a photosensitizer and polymeric lipid DSPE-mPEG2000 dissolved in an organic solvent at a molar ratio of 1.0:10.0 to prepare a mixed solution;
   (2) removing the organic solvent from the mixed solution prepared in the step (1) and drying the resultant to prepare a polymeric lipid film;
   (3) simultaneously hydrating and sonicating the polymeric lipid film prepared in the step (2) in one or more solutions selected from the group consisting of water, PBS, HBS, and HBG at room temperature to 100° C. to form nanoparticles having a micelle structure; and
   (4) filtering the nanoparticles having the micelle structure formed in the step (3) to homogenize, wherein,
   the nanopreparation having the micelle structure has a diameter in a range between about 5.0 to 12.0 nanometer, and
   an incorporation efficiency of the photosensitizer of greater than about 80%.

2. The method as set forth in claim 1, wherein the organic solvent of the step (1) is one or more solvents selected from the group consisting of chloroform, dimethyl sulfoxide, dimethylformamide, ethanol, methanol, tetrahydrofuran, toluene, xylene, and hexane.

3. The method as set forth in claim 1, wherein the photosensitizer is hypericin.

4. The method as set forth in claim 1, further comprising:
   (5) after step (4), performing aging in one or more solutions selected from the group consisting of PBS, HBS, and HBG, when said one or more solutions used in step (3) is water.

5. The method as set forth in claim 1, wherein the filtering of the step (4) comprises:
   (A) filtering the nanoparticles having the micelle structure formed in the step (3) by a filter of 0.05 to 0.20 μm; and
   (B) re-filtering the nanoparticles filtered in the step A by a centrifugal filter of 20 to 40 K.

* * * * *